United States Patent
Cięciara et al.

(10) Patent No.: US 11,534,412 B2
(45) Date of Patent: Dec. 27, 2022

(54) APPLICATION OF TOTAROL AND PHARMACEUTICAL COMPOSITION CONTAINING TOTAROL

(71) Applicant: Emergopharm SP. Z O.O. SP.K., Konstancin-Jeziorna (PL)

(72) Inventors: Mariusz Cięciara, Konstancin-Jeziorna (PL); Artur Wrzosek, Tomice (PL)

(73) Assignee: EMERGOPHARM SP. Z O.O. SP.K., Konstancin-Jeziorna (PL)

(*) Notice: Subject to any disclaimer, the term of this patent is extended or adjusted under 35 U.S.C. 154(b) by 214 days.

(21) Appl. No.: 16/629,005

(22) PCT Filed: Jul. 4, 2018

(86) PCT No.: PCT/PL2018/000066
§ 371 (c)(1),
(2) Date: Jan. 6, 2020

(87) PCT Pub. No.: WO2019/009739
PCT Pub. Date: Jan. 10, 2019

(65) Prior Publication Data
US 2020/0289429 A1    Sep. 17, 2020

(30) Foreign Application Priority Data
Jul. 6, 2017 (PL) .......................... 422140

(51) Int. Cl.
| | |
|---|---|
| *A61K 31/05* | (2006.01) |
| *A61K 47/38* | (2006.01) |
| *A61K 9/00* | (2006.01) |
| *A61K 9/06* | (2006.01) |
| *A61K 9/14* | (2006.01) |
| *A61K 9/20* | (2006.01) |

(52) U.S. Cl.
CPC ............... *A61K 31/05* (2013.01); *A61K 47/38* (2013.01); *A61K 9/0036* (2013.01); *A61K 9/06* (2013.01); *A61K 9/146* (2013.01); *A61K 9/20* (2013.01)

(58) Field of Classification Search
CPC ...... A61K 31/05; A61K 47/38; A61K 9/0036; A61K 9/06; A61K 9/146
See application file for complete search history.

(56) References Cited

U.S. PATENT DOCUMENTS

| | | | | |
|---|---|---|---|---|
| 2003/0153629 A1* | 8/2003 | Syverson | ............. | A61K 9/0034 514/731 |
| 2009/0312279 A1* | 12/2009 | Mookerjee | ............. | A61K 36/06 514/40 |
| 2016/0157483 A1* | 6/2016 | Wendel | ................. | A01N 31/08 424/423 |

FOREIGN PATENT DOCUMENTS

| | | |
|---|---|---|
| CN | 104688810 A | 6/2015 |
| JP | 2011105635 A | 6/2011 |
| WO | 2013089721 A1 | 6/2013 |

OTHER PUBLICATIONS

International Search Report issued in connection with PCT Application No. PCT/PL2018/000066, dated Nov. 6, 2018.
Reinbold Jochen et al., "Development and in vitro characterization of poly (lactide-co-glycolide) microspheres loaded with an antibacterial natural drug for the treatment of long-term bacterial infections." Database Medline, US National Library of Medicine (NLM), Bethesda, Maryland, United States, 2016.

* cited by examiner

*Primary Examiner* — Genevieve S Alley
(74) *Attorney, Agent, or Firm* — Dennemeyer & Associates; Steven M. Shape

(57) ABSTRACT

The invention relates to application of totarol for production of a preparation for treatment of vaginal mucous membrane inflammations of bacterial origin, for alleviation of symptoms in such a treatment, and for prophylaxis and prevention of relapses of such inflammations. The invention includes also a pharmaceutical composition for treatment of vaginal mucous membrane inflammations of bacterial origin, for alleviation of symptoms in such a treatment and for prophylaxis and prevention of relapses of such inflammations, the composition containing from 75 to 95 parts by wt. of a cellulose derivative, from 0.5 to 5 parts by wt. of lactic acid, from 0.5 to 5 parts by wt. of a basic polymer, wherein the stoichiometric ratio of lactic acid to the basic polymer is comprised in the range of 1:1 to 8:1, and comprising totarol in an amount of 0.001 to 5 parts by wt. as the active substance.

8 Claims, 2 Drawing Sheets

APPLICATION OF TOTAROL AND PHARMACEUTICAL COMPOSITION CONTAINING TOTAROL

CROSS-REFERENCE TO RELATED APPLICATIONS

This is a 35 U.S.C. 371 National Stage Patent Application of International Application No. PCT/PL2018/000066, filed Jul. 4, 2018, which claims priority to Polish application P.422140, filed Jul. 6, 2017, each of which is hereby incorporated by reference in its entirety.

BACKGROUND

The invention relates to application of totarol to prevent disturbances in the composition of vaginal bacterial flora and to a pharmaceutical composition containing totarol as the active ingredient. The composition is intended for use in gynaecology and obstetrics during antibacterial, antifungal, antiprotozoan and mixed therapies, and as an regulatory agent of acidity of vaginal environment. The composition may be used as a pharmaceutical preparation or a medical product.

The most frequent inflammatory condition within female birth canal is bacterial vaginosis (BV) being a disturbance of natural bacterial microflora. It is estimated that the frequency of occurrence of this disease entity in females in their puberty amounts to 10-40%. During the course of BV, an abundance decrease or even a total population decay of bacilli of the *Lactobacillus* genus occurs, resulting in uncontrolled multiplication of strictly anaerobic bacteria. The type of bacilli of the *Lactobacillus* genus, their abundance and the amount of glycogen stored in vaginal epithelial cells, transformed by these bacteria into lactic acid, regulate and are responsible for maintaining a proper level of vaginal pH. The reaction of vagina depends on the total amount of organic acids produced by these bacteria, the most important of which is lactic acid mentioned above. Controlled production of these acids causes a vaginal pH value below 4.5, which is necessary for adhesion of bacteria of the *Lactobacillus* genus to the vaginal epithelium and enables to maintain its correct microflora in qualitative and quantitative respects. Thus, the correct microflora inhibits growth of microorganisms requiring environments with pH>4.5 for their presence. Thereby, the physiological microflora protects from infections by pathogenic microorganisms also by competition for nutrients and receptor sites on the cell surface, and stimulates the immune system of genital tract to produce antibodies cross-reacting with other microorganisms.

The most frequently isolated pathogen being the main cause of BV is *Gardnerella vaginalis*, occurring almost in all females suffering from this condition, similarly as another anaerobe, *Atopobium vaginae*, as well as occurring in 50% of the BV cases *Mobiluncus* spp. *bacilli*.

An ability of multiplicating pathogenic bacteria to form a multibacterial biofilm, adhering to the vaginal epithelium, is a particularly important feature impeding the therapy in the BV course. Colonies of the biofilm-forming bacteria, containing *Gardnerella vaginalis* and *Atopobium vaginae* as main components, exhibit an ability to adhere to wet surfaces and to each other. Formation of the biofilm matrix is aimed for protection of the microorganisms forming it from a degradative impact of natural factors of the vaginal environment and from the influence of pharmacological agents, including antibiotics. A compact biofilm structure is highly difficult to remove from vaginal walls. Presence of a biofilm adhering to epithelial cells, wherein the *Gardnerella vaginalis* bacteria constituted 90%, was shown in biopsy in females with BV.

The phenomenon of biofilm formation by the pathogens, lack of inflammation features in BV, cases of incorrect BV diagnosis reaching 61% (identification of BV according to the Amsel criteria is cheap, easy and possible to carry out in practically every gynaecological office; however it has disadvantages of evaluation subjectivity and a lower repeatability factor, depending on the experience of the physician), and a group of patients in which the BV has a symptomless character lead to relapses in the majority of the treated patients after 12 months.

The above-described features and mechanisms occurring in the BV course are extremely important from the medical point of view, because of the fact that the bacterial vaginal infection is considered one of the etiological factors of spontaneous abortions, premature deliveries, intrauterine infections, premature escapes of amniotic fluid, intrauterine growth restriction (IUGR), inflammations of uterine mucosa and organs of smaller pelvis. Also, BV may be a cause of other perinatal infections, dangerous to an equal degree for the infected mother and the newborn.

Another condition connected with disturbances in qualitative and quantitative composition of vaginal microflora consists in a vaginal inflammation caused by microorganisms existing under aerobic conditions, called aerobic vaginitis (AV). In AV, a decrease in the number or lack of bacteria of the *Lactobacillus* genus is also observed, as well as growth of a mixed vaginal flora, with composition dominated by cocci of Gram-positive streptococci of group B: *Streptococcus agalactiae, Enterococcus fecalis, Staphylococcus aureus*, and bacilli of Gram-negative bacteria: *Escherichia coli*. Similarly as in the case of BV, identical changes are observed here too. Concentration of lactates in the vaginal content decreases, vaginal pH value increases to >6.0, and also concentration of pro-inflammatory cytokinins increases. Because of the lack of unambiguous diagnostic criteria and co-occurrence of other infections, such as mycosis and trichomonadosis, the frequency of occurrence of AV is not defined precisely.

The occurrence of disturbances in the composition of vaginal microflora is a cause of inflammations within the genital tract, which may be caused by two completely different kinds of pathogenic bacteria existing under extremely disparate oxygenic conditions. An abnormal biocoenosis and inflammations may also lead to development of inflammatory postoperative complications, particularly gynaecological, obstetrical and urological. They pose a huge threat for a foetus too, whose organism is devoid of the contact with microorganisms in the period of intrauterine life, but while passing through the birth canal, it is colonised by the vaginal microflora of its mother.

The majority of currently used treatment regimens is based mostly on metronidazole, tinidazole, and, in the case of BV, clindamycin. These substances are commonly and routinely applied in the form of oral or intravaginal. The fundamental advantages of metronidazole consist in its activity against both aerobic, and anaerobic bacteria, and the fact that anaerobic lactic acid bacilli of the *Lactobacillus* genus are completely resistant to this antibiotic. Moreover, this drug is inexpensive, easily accessible and well-tolerated by the patients usually. Unfortunately, report on the resistance of *Gardnerella vaginalis* to the action of this chemotherapeutic agent appear more and more often in global scientific literature, indicating also an increasing percentage of resistant strains of the species. Studies carried out by Goldstein et al. in 1993 shown the metronidazole-resistant strain percentage on the level of 20%, while just in 2002, the same group of researchers found an increase in the percentage of resistant strains to the level of 29%. The most recent reports indicate that the process of acquiring resistance to metronidazole intensifies with a significant rate. In drug resistance studies carried out and published in 2007, a resistance of *Gardnerella vaginalis* strains to metronidazole reaching even 70% was observed. Studies carried out in Poland on a collection of 67 strains isolated from a group of 604 females confirmed that 68.7% (46 out of 67) of the studied strains were characterised by resistance to metronidazole. The alarming increase in the number of BV-related anaerobic strains exhibiting the described mechanism of resistance to metronidazole may result in a necessity to change the treatment regimens for bacterial vaginosis in several years.

In comparison to metronidazole, clindamycin is characterised by a higher effectiveness against anaerobic Gram-negative bacilli, with a simultaneous limited activity against bacteria existing under aerobic conditions. Additionally, a negative consequence of use of this drug is its high activity against and ability to inhibit growth of bacteria of the *Lactobacillus* genus, which may disturb the process of regeneration of a normal vaginal ecosystem, and as a result, lead to secondary fungal infections of vulva and vagina, caused by *Saccharomycetes* of the *Candida albicans* and *Candida glabrata* species.

Amoxicillin with clavulonic acid is proposed as a second-line drug in the BV treatment. Unfortunately, the literature is lacking data on evaluation of effectiveness of this antibiotic in treatment of vaginal infections caused by anaerobic bacteria.

Despite the high effectiveness of the described antibiotics, relapses of vaginal and birth canal infections of bacterial origin are observed quite often. This phenomenon is evident particularly in the case of BV patients. It is estimated that approx. 30% of females will suffer from renewed clinical symptoms of BV after 3 months, and approx. 80%—within the first year from the completion of therapy. Resistance of the anaerobic bacteria strains to the antibiotics used, together with a simultaneous high antibacterial activity against the lactic acid bacilli of the *Lactobacillus* genus naturally occurring in the vaginal microflora, necessary for its proper functioning, are indicated as one of the main causes of the relapses.

An important problem consists in changes in structures of bacteria constituting the main cause of infections of vaginal mucous membranes. The scope of changes occurring in pathogenic microorganisms, aimed for evolving new resistance mechanisms, is multidirectional and multilevel. Frequently, a single pathogen uses several mechanisms for protection from a vast range of commonly applied therapeutic preparations.

Thus, it is hard to anticipate currently the range of antibacterial activity of a given substance, active against the pathogenic microorganisms with a so-variable structure, despite its commonly known activity against the pathogens already tested. It was observed that the activity of a therapeutic substance may vary in time, and in some cases, even decay under the influence of newly-evolved defence mechanisms of the pathogen.

Therefore, a change in the activity, including its complete decay, and limitation of the activity range for pathogens of various kinds, are serious problems of the currently applied treatments, both in the case of BV-type, and AV-type infections. The increasing incidence of resistance of the *Gardnerella vaginalis* bacterium to metronidazole limits the possibility of effective treatment of BV, and probably, contributes into the increase in frequency of relapses of clinical symptoms.

An important role in treatment of inflammations of vaginal mucous membranes, particularly those of a mixed character: BV+AV or BV together with the accompanying secondary fungal infection, may be played by compounds of natural origin. A broad range of antibacterial activity, both against aerobic, and anaerobic bacteria, is a necessary condition determining the therapeutic usefulness in treatment of resistant cases or mixed infections. Also, the influence of the new substance on the physiological component of the natural vaginal bacterial microflora, namely the lactic acid bacteria of the *Lactobacillus* genus, should be taken into account.

Antibacterial activity of a tricyclic diterpene with a generic name "totarol", having a chemical structure shown in the formula 1.

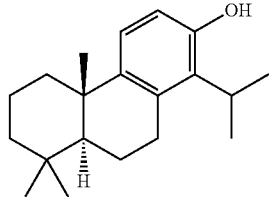 [SMILES: CC(C)c1c(O)ccc2c1CC[C@H]1C(C)(C)CCC[C@]21C]

It is a compound of natural origin, found in an endemic tree species *Podocarpus totara* (totara), which occurs in the territory of New Zealand.

Antibacterial activity of totarol is disclosed in a number of scientific papers and patent publications. "*Antibacterial activity of totarol and its potentiation*" *Journal of Natural Products* Vol. 55, No. 10, pp. 1436-1440, October 1992 describes a high effectiveness of totarol-containing extracts against Gram-positive bacteria: *Bacillus subtilis, Brevibacterium ammoniagenes, Streptococcus mutans, Propionibacterium acnes*, and *Staphylococcus aureus*. "*Clinical report on the Efficacy of Totarol and Totarol in Combination with Tea Tree Oil as an Antimicrobial Against Gram-negative Bacteria*" prepared for Mende-DEK Ltd. November 2003 confirms the effectiveness of totarol against four Gram-negative bacteria: *Salmonella menston, Escherichia coli, Enterobacter aerogenes, Pseudomonas aeruginosa* and one Gram-positive bacterium: *Enterococcus fecalis*. "*The synthesis and antibacterial activity of totarol derivatives. Part 1: modifications of ring-C and pro-drugs*" *Bioorganic & Medicinal Chemistry* 1999, 7(9): 1953-1964 describes its activity against a Gram-positive bacterium *Streptococcus pneumoniae*. The publications cited above contain information on the bacteria totarol is active against, as well as indicate a quite large group of pathogenic bacteria, against which totarol does not exhibit any antibacterial activity. The latter are often pathogens of the same genus, for which activity of totarol has been found, illustrating nonobviousness and individuality of the impact on the respective microbial strains.

From the description of Japanese Patent Application No. JP 01311019, activity of totarol against Gram-positive bacteria, in preparations intended for external use. In turn, the description of Patent Application No. WO2005073154 presents a method of totarol extraction from plant material, and a preparation produced from totarol obtained by the method according to the Application. In this description, it has been proved that totarol acts also against Gram-negative bacteria. Composition of the preparation, its form and application were disclosed in this Application in a very general way, without indicating its specific purpose. The description of Patent Application No. WO2014137231 discloses application of totarol-containing preparations for treatment of inflammation of mammary gland, uteritis, and wounds. The description of Patent Application No. CN104027260 discloses application of preparations in the form of a toothpaste or a mouthwash fluid for treatment of wounds in oral cavity.

So far, no antibacterial activity of totarol against pathogenic bacteria being main causes of infections of vaginal mucous membranes has been proved. They are a Gram-variable anaerobic bacterium *Gardnerella vaginalis* responsible for BV infections and a Gram-positive aerobic bacterium *Streptococcus agalactie* causing infections of the AV type.

As a result of studies using clinical strains isolated from human female birth canals, carried out by the present inventors, it turned out that totarol exhibits an unusually high activity against the mentioned pathogens at a very low MIC concentration. The activity both against the clinical strain of the pathogenic anaerobic bacterium *Gardnerella vaginalis*, and the clinical strain of the aerobic bacterium *Streptococcus agalactie* causes that—which is highly valuable—the activity spectrum of totarol overlaps with the activity spectrum of metronidazole having a dramatically increasing resistance of the microorganisms mentioned above, which limits, or even precludes the effective medical use of the latter.

So far, also the impact of totarol on the lactic acid bacilli of the *Lactobacillus* genus was unknown. For the first time, such a study has been carried out by the present inventors. It has turned out completely unexpectedly that despite the fact that the bacilli of the *Lactobacillus* genus are, such as *Gardnerella vaginalis*, representatives of anaerobic bacteria, there is a significant, approximately 10-fold difference in values of MIC concentrations for these microorganisms, which is best illustrated by the following Table.

| | Strain name | | | | |
|---|---|---|---|---|---|
| | E. faecalis | S. agalactiae | G. vaginalis | L. plantarum | L. gasseri |
| MIC value | 0.0025% | 0.0013% | 0.005% | 0.08% | 0.04% |

It is the nonobvious, and at the same time, critical for the subject of the invention, difference between the effective concentrations for the individual bacteria of the same genus which determines the uniqueness and exceptional quality of totarol in the application described.

New and unique properties of totarol, discovered by the present inventors for the first time, decide on its huge medical potential in use being the subject of this Application. Low MIC concentrations with a simultaneous high antibacterial effectiveness, against the bacteria being the main cause of both BV, and AV, does not exhibit activity for, and thus a negative impact on co anaerobic bacilli of the *Lactobacillus* genus, being the main component of a physiologically correct vaginal bacterial microflora. This unique mechanism of totarol action decides on its vast therapeutic usefulness in treatment of vaginal infections of bacterial origin. The lack of activity against lactic acid bacilli in the corresponding MIC range prevent additional sterilisation of vaginal microflora, simultaneously creating optimum conditions for growth of these bacteria. An increase in the concentration of lactic acid bacilli conditions the natural restoration of vaginal protective barrier, thereby preventing relapses of clinical symptoms and protecting the vaginal environment from secondary fungal infections, which accompany a classical therapy using clindamycin.

Apart from the aforementioned new and unexpected properties of totarol, their huge therapeutic potential is determined by a lack of the resistance mechanism occurring in the case of metronidazole.

The high therapeutic usefulness and safety in gynaecological applications has been confirmed additionally by the present inventors by tissue studies evaluating the impact of totarol on human vaginal epithelial cells using the A-431 cell line, carried out for the first time. The tests carried out have not proved apoptotic and necrotic action of the tested substance on human vaginal epithelial A-431 cells within a broad range of incubation times (2-24 hours).

The test results confirming the broad antibacterial activity spectrum for specific, strictly defined MIC concentrations of totarol, with a simultaneous lack of activity against lactic acid bacilli of the *Lactobacillus* genus and lack of negative influence on human vaginal epithelial cells, obtained by the present inventors for the first time, have became a basis for application of totarol according to the invention. The application according to the invention is a result of studies carried out by the present inventors, indicating that totarol is active against clinical strains of *Gardnerella vaginalis* and *Streptococcus agalactie*, isolated from human female birth canal. The studies were carried out based on the methodology described in the "*Determination of the Minimum Concentration of Totarol & Antibiotics Required to Inhibit and Kill Growth of Staphylococcus aureus in Broth Cultures*" (Project NZC-MEND-1312) document. The results and methods for carrying out the described studies is presented in detail in the examples of the invention.

However, totarol has limitations resulting from physicochemical properties of the substance. Hydrophobic character of its molecule, resulting in a complete lack of solubility in water, is a fundamental technological problem, precluding an effective application of the substance in gynaecological compositions. Because of the target application spot of the pharmaceutical composition, namely the vaginal mucous membrane, use of most organic solvents, dissolving totarol, has turned out to be impossible. Solvent belonging to alcohols, such as ethanol, or polyhydric alcohols, such as propylene glycol, exhibit a strong irritating effect, and adding water to them results in precipitation of the dissolved totarol. Use of halogen derivative solvents, such as, e.g., methylene chloride or chloroform, is also impossible, because of their toxic character. Embryotoxic and teratogenic properties of N,N-dimethylformamide disqualify its use as a component of pharmaceutical compositions. DMI, applied in in vitro studies, is used in pharmaceutical industry, but only in production of medical products for external use, such as steroid ointments.

As the composition of vaginal microflora may change under the influence of the applied antibiotics, endocrinally or immunologically-active agents during pregnancy or menopause supportively, use of lactic acid in the form of vaginal gel is recommended, particularly after completion of a pharmacological BV treatment.

Polish Patent Specification No. pl 166898 discloses a method for production of a methylcellulose-lactic acid complex, consisting in solvation of methylcellulose with lactic acid in the form of a solution composed of 5-25 parts by wt.

of lactic acid and 10-20 parts by wt. 95% of ethyl alcohol. The solution is sprayed onto 75-95 parts by wt. of methylcellulose with continuous mixing, and then the product is subjected to drying, removing the ethyl alcohol. The obtained powder is pelletized. Lactic acid binds methylcellulose, forming a binary complex. Methylcellulose solvated with lactic acid has properties of rapid water fixing, forming a gel with viscosity, adhesive and coating properties similar to those of mucus produced in the vagina under physiological conditions. Compositions using lactic acid only, having action based on adjustment of pH, are insufficient in the case of treatment of vaginal infections, and may be used only for prophylactic purposes or to maintain good hygiene of birth canal of healthy females.

From Patent Description Nos. pl 194437, p1201868 and pl 201869, a method for production and compositions using a methylcellulose-lactic acid complex are known, wherein single strains of lactic acid bacteria: *Lactobacillus crispatus, Lactobacillus jenseni, Lactobacillus rhamnosus, Lactobacillus gasseri, Lactobacillus helveticus* are used additionally as active substances, in the form of a lyophilisate. The composition comprises from 75 to 95 parts by wt. of methylcellulose, from 0.5 to 5 parts by wt. of lactic acid, from 0.5 to 5 parts by wt. of a basic polymer, preferably Eudragit or chitosan, or polyvinylpyrrolidone, or their mixtures, and from 0.5 to 5 parts by wt. of *Lactobacillus* bacterial lyophilisate, the stoichiometric ratio of lactic acid to the basic polymer comprising in the range of 1:1 to 8:1. It is preferable that the composition comprises a culture medium in the amount of 5 to 10 parts by wt., in the form of monosaccharides or polysaccharides. The method for production of this known composition consists in preparation of a binary component by dissolving a basic polymer in a solution of lactic acid, in a stoichiometric ratio to free amine groups in the basic polymer within the range of 1:1 to 8:1, mixing to a complete dissolution of the basic polymer, and then, ethyl alcohol is added in an amount not smaller than 5 parts by wt., mixed to a complete homogeneity, and the so-prepared mixture is sprayed onto methylcellulose and mixed, until its uniform wetting is achieved. The obtained product is subjected to drying, during which the ethyl alcohol evaporates, and a *Lactobacillus* bacterium lyophilisate is added to the so-obtained dry powder.

The goal of vaginal administration of the single strains mentioned above is to provide optimum conditions for a complete restoration of physiological vaginal bacterial flora. Simultaneously, the authors of the mentioned patent descriptions emphasise that reproductive organs, similarly as other human anatomical regions, have numerous "ecological niches", and consequently, vaginal fornix, cervix channel, cervical external wall, and frontal section of the vagina have all different bacterial floras. The described differences in the composition of the bacterial flora cause a decrease in the effectiveness of the described compositions containing a single strain of bacilli of the *Lactobacillus* genus. Use of a larger number of strains in a single composition is not preferable in the light of current studies, because it may lead to a too high concentration of these bacteria, which in consequence is a cause of cytolytic vaginitis, often erroneously diagnosed and treated as vaginal candidiasis.

The raw material in the form of bacterial lyophilisates has numerous severe limitations resulting from the specificity of a material containing living organisms, and its application under technological conditions is connected with a series of difficulties. Parameters of a probiotic raw material are characterised by a high variability, strictly dependent on numerous parameters of realisation of the fermentation process. Obtaining the final raw material of a high purity requires use of substances increasing the viability of microorganisms and stabilising the fermentation process, as well as complicated and expensive purification and lyophilisation methods. The number of colony forming units (CFU) in the bulk of the obtained raw material depends strictly on both the kind of the bacterial strain, and the method and parameters of realisation of the whole production process. This number is decreasing constantly in time, because the stability and viability of the probiotic strains depend on temperature, storage conditions, and water contained in them. It affects adversely the viability and stability of the bacterial features during storage and distribution of probiotic products.

The production process of ready-made pharmaceutical agents containing probiotic raw materials must be realised in separated production lines using dedicated machinery, because the quality control systems and GMP (Good Manufacturing Practice) guidelines obligatory in the pharmaceutical industry classify these raw materials as severe source of microbiological pollution. The necessity to use dedicated manufacturing equipment results from a high risk of colonisation and from the fact that the regularly used cleaning procedures do not warrant achieving a proper purity. It may be achieved only by use of advanced and expensive cleaning and sterilisation methods, which include dismantling the individual working elements contacting with the manufactured product. The cleaning and sterilisation procedures are subject to a complicated validation process confirming their efficacy and repeatability, and the lack of even small amounts of the applied aggressive cleaning substances in the clean equipment.

The aim of the invention was to solve the problems defined above.

The essence of the invention consists in application of totarol for production of a preparation for treatment of vaginal mucous membrane inflammations of bacterial origin, and for alleviation of symptoms in such a treatment. In particular, the application according to the invention relates to bacterial vaginosis (BV) and aerobic vaginitis (AV).

Preferably, totarol in the application according to the invention is used in the form of a composition containing from 75 to 95 parts by wt. of a cellulose derivative, preferably methylcellulose, from 0.5 to 5 parts by wt. of lactic acid, from 0.5 to 5 parts by wt. of a basic polymer, preferably an acrylic polymer, most preferably a copolimer of methacrylic acid and ethyl acrylate, or chitosan or polyvinylpyrrolidone or their mixtures, wherein the stoichiometric ratio of lactic acid to the basic polymer is comprised in the range of 1:1 to 8:1. In accordance with the invention, the active substance in the composition is totarol in an amount of 0.001 to 5 parts by wt.

The composition may contain also a culture medium for probiotic bacteria in the amount of 5 to 10 parts by wt. in the form of monosaccharides or polysaccharides. The composition may contain also additional active components, in an amount of 0.001 to 10% by wt., depending on the component type.

The composition according to the invention is produced by the method known from prior art (PL194437, p1201868, p1201869), wherein totarol is being added to alcohol. In more detail, the basic polymer is dissolved in a solution of lactic acid, in a stoichiometric ratio to free amine groups in the basic polymer in the range of 1:1 to 8:1, the solution is mixed to a complete dissolution of the basic polymer, then a primary alcohol is added in an amount not smaller than 5 parts by wt. together with dissolved totarol, mixed to a complete homogeneity, and the so-prepared mixture is applied onto the surface of cellulose derivative particles, mixing to a uniform wetting. The obtained product is subjected to drying, during which, the primary alcohol is removed, and then, the product is dosed into containers or subjected to further processing to a desired form.

DETAILED DESCRIPTION OF THE DRAWINGS

Figure 1:
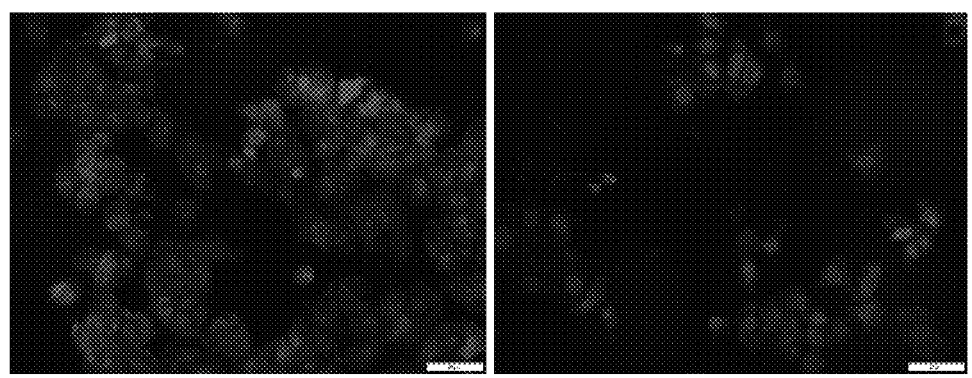
FIG. 1—from the left: Necrotic cells (magnification 400×) after 8 h of incubation with $H_2O_2$; from the right: Necrotic cells (magnification 400×) after 24 h of incubation with $H_2O_2$.

The composition in accordance with the invention is intended for use in prevention and treatment of inflammations of vaginal mucous membrane. It is characterised by a high effectiveness and selectiveness of antibacterial activity, due to application of a strictly defined amount of totarol as the active substance. Additionally, the composition may contain substances exhibiting antifungal and antiprotozoan activity.

The most important, unique advantage of the composition according to the invention in its described form is the fact that the highly selective antibacterial activity of totarol, directed against pathogenic bacteria, does not infract the proper biocenosis and does not destroy lactic acid bacilli of the *Lactobacillus* genus, being the most significant component of the physiological flora. An additional agent stimulating growth and restoration of correct vaginal flora is constituted by lactic acid, which, due to its regulating function of lowering the pH, forms a barrier against microbes sensitive to acidic environment and creates favourable conditions for growth of bacteria of the *Lactobacillus* genus.

In the solutions used currently, the therapeutic substance in the form of an antibiotic destructs the pathogenic flora, simultaneously destroying the physiological flora and the lactic acid bacilli being the main component of the latter. The pharmaceutical composition according to the invention, due to the presence of an antibacterially active totarol concentration, determined experimentally, acts in a specific and selective way, only on pathogenic bacteria being the cause of the inflammation resulting from BV or AV. This concentration was determined as a result of a research process, carried out by the present inventors for the first time. Additional presence of lactic acid in the composition, buffered with a basic polymer, acidifies the environment and support growth and development of existing *Lactobacillus* bacteria. Due to this fact, the composition exhibits a very high effectiveness with a simultaneous lack of adverse impacts on the physiological biocenosis, which limits disease relapses recorded with the majority of patients after BV or AV, occurring in the case of application of classic therapies. Simultaneously, the known possibility for exact pH adjustment by changing the ratio of lactic acid to the basic polymer may be utilised in the composition. The composition adheres well to the whole surface of the mucous membranes, which extends its residence time inside the vagina and provides a uniform contact with the antibacterial agent in the form of totarol.

The composition to be applied in the case of mixed infections may be obtained by supplementing the basic constitution of the composition with substances having profiled antifungal or antiparasitic activity, while selecting a pH proper for the treatment. The composition may be used also for prophylactic purposes or as a product for daily intimate hygiene. The composition in the form of a loose powder may be used for direct gynaecological treatments as a dusting powder or for making preparations in other forms, such as gels or vaginal solutions, after adding a properly selected amount of purified water, or for production of tablets after mixing with known substances which enable pelletizing, or pessaries. The target constitution of all mentioned final preparation may be supplemented with substances exhibiting antifungal or antiprotozoan activity.

By the method according to the invention, a composition with a selective antibacterial activity directed only against pathogenic bacteria is obtained. Due to the uniform application of totarol on particles of a chemically modified cellulose derivative, an effect of development of surface of the contact of the active substance with the mucous membrane in the whole volume of the used preparation is achieved. Also, this solution allowed for significant limiting, and in some cases—eliminating of the necessity to use of large amounts of water-miscible organic solvents in the final products, in order to dissolve the hydrophobic totarol. Simultaneously, as a result of buffering effect of the basic polymer used, an effect of gradual and prolonged release of the active substance together with the lactic acid adjusting the vaginal pH is achieved. The described activity was not possible to obtain using the complex known from the patent descriptions Nos. pl 166898, 194437, 201868, and 201869. The composition produced by the method according to the invention provides its good adhesion to the whole surface of the mucous membranes, which extends its residence time inside the vagina and provides a uniform contact with the antibacterial agent in the form of totarol.

The invention includes also use of the composition defined above for production of a preparation for supportive treatment and alleviation of symptoms in treatment of vaginal mucous membranes' inflammations of bacterial origin. The composition is particularly useful in the case of relapsing infections of the vaginal mucous membrane.

The invention is presented in more detail in the examples.

Example 1

Test of antibacterial activity of totarol using DMI (dimethylisosorbide) as a solvent.

A suspension of 0.5 McF in physiological saline (suspension density $10^8$ cfu/ml) was prepared from a 24-hour culture of a standard strain. 1 ml of the suspension was collected to 9 ml of a TSB broth (dilution $10^-$). Suspensions with a dilution of $10^{-6}$ were prepared in the described way. A suspension with a cell density of $10^5$ cfu/ml was selected for further investigations. For each strain, 2 96-well plates were prepared: the first one was intended for the OD measurement, the second one—for quantitative culture on solid media.

A/ to wells B1-D1, B2-D2 and B-D 4-11, 100 pl of the broth were added;
B/ to wells B3-D3, 200 pl of the broth were added;
C/ to wells B1-D1, 1 pl of stock I was added;
D/ to wells B2-D2, 1 pl of stock II was added;
E/ to wells B3-D3, 2 pl of stock III were added.

Using a multichannel pipette, 100 pl of the sample were collected from each of the B3-D3 wells and placed in wells B4-D4 (mixing by sucking the content in and letting it out for 5 times). The pipette tips were replaced and 100 pl of the content were collected from of the B4-D4 wells, and placed in wells B5-D5, mixing as previously. These operations were repeated through the wells B11-D11. The content in the B11-D11 wells was mixed, and 100 pl of the fluid were collected and discarded. This way, a series of dilutions of totarol samples in DMI in the range of 0.32% to 0.0004% was obtained. Then, 100 pl of a corresponding bacterial culture were added to the wells B, C, D 1-11. In consequence, a change in the final concentration range occurred, to 0.16%-0.0002%.

Control Preparation:
Negative control: 100 pl of the broth+1 pl DMI were added to the A1 well.
Positive control (I): 100 pl of the broth with the bacterial culture were added to the wells E1-G1.
Diluent positive control (II): 100 pl of the broth with the bacterial culture+1 pl DMI were added to the wells E2-G2.

The OD value in the individual wells was read at the wavelength of 620 nm (read time 0). From the second 96-well plate, a culture was inoculated by a quantitative method from every dilution onto a well with a proper solid medium, and incubated for 24 h at 37° C. under aerobic or anaerobic conditions, depending on the strain. The plates were incubated under aerobic conditions or in an atmosphere of an elevated $CO_2$ concentration (for the strains requiring it) in an incubator at 37° C. The OD was read after 8 h, 16 h, and 24 h, respectively. Before every OD measurement, the contents of the wells were mixed delicately. In parallel to the OD readout, cultures we inoculated from the second 96-well plate, from every dilution, into plates with a proper solid medium, and incubated for 24 h at 37° C., under aerobic or anaerobic conditions. For the analysis of the experimental results, an average value of the OD measurement obtained from three repetitions in the individual times (0, 8, 16, and 24 h) for the individual microbes (*Gardnerella vaginalis, Streptococcus agalactiae, Enterococcus faecalis, Lactobacillus gasseri/plantarum*) was taken. Additionally, the number of bacteria grown on solid media was taken into account. The results are presented in Tables 1, 2, 3, 4, and 5. The results of the tests confirm the specific, concentration-dependent selectiveness, and the high antibacterial effectiveness of totarol against the pathogenic microorganisms: *Gardnerella vaginalis, Streptococcus agalactiae, Enterococcus faecalis* at low MIC values safe for bacteria of the *Lactobacillus* genus.

Example 2

Test of totarol impact on the human vaginal epithelial cells of the A-431 cell line (ATCC® The study was carried out using the following test: Annexin-V-Fluos (Roche, Mannheim, Germany), during incubation for 2, 8 and 24 hours, under in vitro conditions, according to the instructions of the test's manufacturer. The totarol sample was prepared by dissolution of 3 mg of totarol in 3 ml of 100% DMI.

The cultivation time for the A-431 cell line was 20 days. The culture was carried out at a temperature of 37° C. in an atmosphere containing 10% $CO_2$, on a DMEM culture medium (Institute of Immunology and Experimental Therapy PAS [IITD PAN], Wroclaw), with an addition of 10% of foetal bovine serum (FBS, Sigma-Aldrich). The culture fluid were being replaced regularly every 48 hours. After achieving a decantable growth or the so-called "monolayer", the cells were passaged using (for approx. 10 min) 0.25% trypsin (Sigma-Aldrich). Then, the obtained tissue line was passed to 24-well plates (TPP), adjusting their densities to the value of $5 \times 10^5$ per well. The tissue culture of the studied lines was carried out for 3 next days on the surface of sterile microscope slides placed on the bottom of a 24-well plate, until a decantable growth was obtained on the surface of the microscope slides. After obtaining the so-called "monolayer", the cells were washed with PBS without $Ca^{2+}$ and $Mg^{2+}$ ions (IITD PAN, Wroclaw), and poured with 700 pl of fresh DMEM medium with 10% FBS, together with 300 µl of properly prepared totarol.

Negative control: 1000 µl of fresh DMEM medium with 10% FBS.
Solvent control: 700 µl of fresh DMEM medium with 10% FBS+300 µl of DMI solvent.
Necrosis positive control: 900 µl of fresh DMEM medium with 10% FBS+100 µl $H_2O_2$ (30%).

Figure 2:
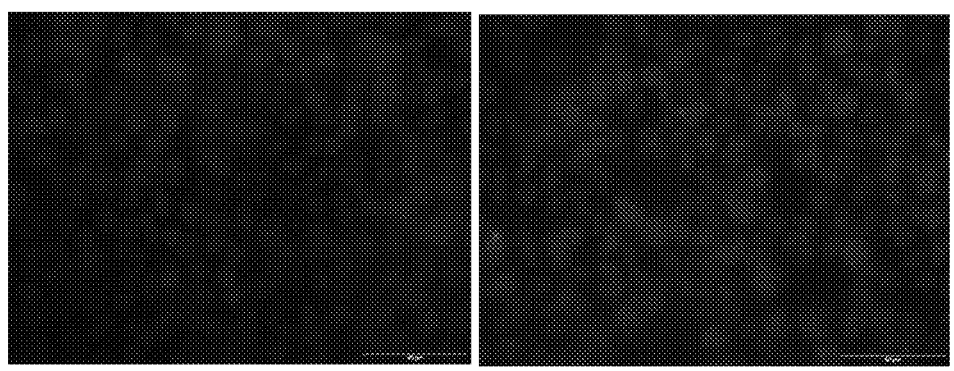
FIG. 2—from the left: No apoptosis and necrosis in epithelial cells (magnification 400×) after 8 h of incubation—negative control; from the right: No apoptosis and necrosis in epithelial cells (magnification 400×) after 24 h of incubation—negative control.
Figure 3:
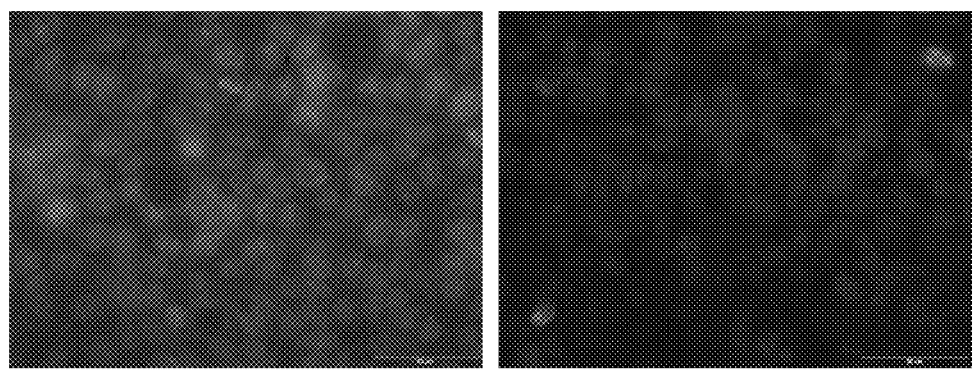
FIG. 3—from the left: No apoptosis and necrosis in epithelial cells (magnification 400×) after 8 h of incubation—solvent control; from the right: No apoptosis and necrosis in epithelial cells (magnification 400×) after 24 h of incubation—solvent control.
Figure 4:
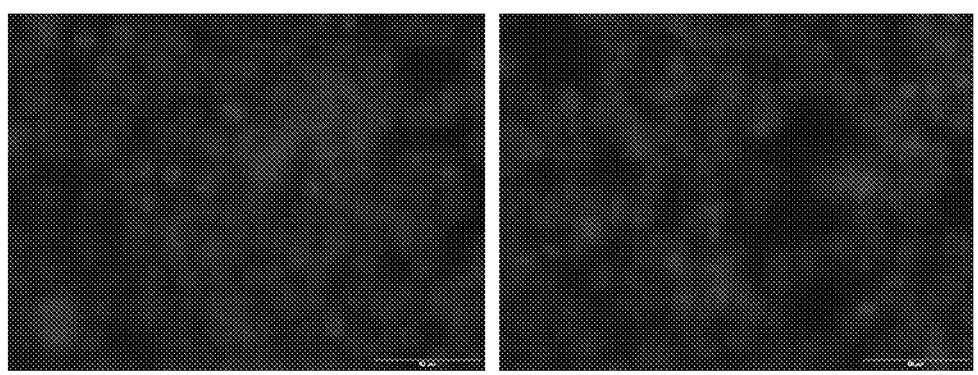
FIG. 4—from the left: No apoptosis and necrosis in epithelial cells (magnification 400×) after 8 h of incubation—totarol; from the right: No apoptosis and necrosis in epithelial cells (magnification 400×) after 24 h of incubation—totarol.

The proper examination using the Annexin-V-Fluos test causes green staining of apoptotic cells. For staining of necrotic cells, propidium iodide (PI) is used. This dye has an ability to penetrate the cell's interior freely only through a damaged cellular membrane, staining the interior red. In the case of a lack of damages of the cellular membrane, propidium iodide remains on its surface, forming a characteristic red "halo" around the cell. After a corresponding study time, i.e. 2, 8, and 24 hours, the culture fluid was removed, the content was washed with PBS (pre-heated to a temperature of 37° C.) twice. Then, 100 µl of the fluorescent stains mixture including in the Annexin-V-Fluos (Roche) kit were applied on the surface of each microscope slide (placed in a culture well) and additionally, Hoechst stain was used (cellular DNA staining). The staining procedure was carried out according to the manufacturer's recommendations. The culture together with the stains applied onto it were incubated at room temperature for 20 min. The intensity of light emitted by the cells stained with the individual stains was observed using a fluorescent microscope at the wavelength of 494-520 nm, using 400× magnification. The cells were counted in five visual fields, and the results were averaged. The reliability of the tests carried out is confirmed by hydrogen peroxide used as a positive control, causing a distinct necrosis process already after 2 hours of incubation. Data analyses were carried out on the basis of the average number of cells from five visual fields in the individual times (2, 8, and 24 h). The results are presented in Table 6 and in the form of photographic documentation—FIGS. 1, 2, 3, 4. The results of the tests prove the lack of apoptotic and necrotic impact of totarol on human vaginal epithelial A-431 cells within a broad range of incubation times (2-24 hours).

Example 3

Preparation of the Composition in the Form of Powder

Composition Ingredients:

| | |
|---|---|
| 1. Totarol | 0.1 parts by wt. |
| 2. Lactic acid | 1.0 parts by wt. (2 moles) |
| 3. Eudragit E-100 | 1.5 parts by wt. (1 mole) |
| 4. Methylcellulose | 97.4 parts by wt. |

The composition is prepared by dissolving Eudragit in lactic acid in a stoichiometric ratio mentioned in the composition's constitution, in a mixer equipped with a mechanical stirrer, mixing for 20 minutes, then leaving the whole mixture for 24 hours. After this time, the obtained component is dissolved in 95% ethyl alcohol, using 10 parts by wt. of the alcohol and 0.1 parts by wt. of totarol per total amount of ingredients. The whole mixture is mixed until the component is dissolved, then the obtained solution is sprayed through a nozzle onto methylcellulose placed in a mixer of a nozzle sprayer, and mixed until the methylcellulose is wetted uniformly, but not shorter than for 10 minutes. The wet product is subjected to drying at a temperature of 25° C. in a dryer with forced air circulation and solvent condenser. During the drying, ethyl alcohol is removed. A loose powder is obtained, which is mixed to a complete homogenisation and dosed to plastic or glass containers.

Example 4

Preparation of the Composition in the Form of Gel

Composition Iingredients:

| | |
|---|---|
| 1. Totarol | 0.5 parts by wt. |
| 2. Lactic acid | 0.5 parts by wt. (1 mole) |
| 3. Chitosan | 0.83 parts by wt. (1 mole) |
| 4. Methylcellulose | 98.2 parts by wt. |
| 5. Purified water | 25 parts by wt. per total amount of ingredients |

The composition is prepared similarly as in Example 3, but water is added with mixing to the obtained dry product in the form of powder, and then, after obtaining a homogeneous mixture, it is left for 30 min without mixing. The obtained gel is dosed into plastic containers with applicators.

Example 5

Preparation of the Composition in the Form of Tablets

Composition Ingredients:

| | |
|---|---|
| 1. Totarol | 0.08 parts by wt. |
| 2. Lactic acid | 0.5 parts by wt. (1 mole) |
| 3. Polyvinylpyrrolidone-90 | 5.0 parts by wt. (1 mole) |
| 4. Methylcellulose | 94.4 parts by wt. |

The composition is prepared similarly as in Example 3, but known substances used in pelletizing are added to the obtained dry product in the form of powder if necessary, and then, the product is pelletized by a known method into proper therapeutic doses.

Example 6

Preparation of the Composition in the Form of Moulded Pessaries

Composition Ingredients:

| | |
|---|---|
| 1. Totarol | 0.5 parts by wt. |
| 2. Lactic acid | 4.0 parts by wt. (8 moles) |
| 3. Chitosan | 0.83 parts by wt. (1 mole) |
| 4. Methylcellulose | 94.4 parts by wt. |

Additives per total amount of composition ingredients:

| | |
|---|---|
| 1. Gelatine | 16.5 parts by wt. |
| 2. Purified water | 83.5 parts by wt. |

The composition is prepared similarly as in Example 3, but the obtained dry product in the form of powder is dissolved in part of the water, giving a gel, to which an aqueous gelatine solution (prepared from the rest of the water), heated to a temperature of 90° C., is added. Then, the product is mixed and poured into moulds, obtaining moulded pessaries.

Appendix

TABLE 1

Determination of the MIC value of totarol against the *Enterococcus faecalis* strain.
*Enterococcus faecalis* - clinical strain
(initial working density $7.0 \times 10^5$ cfu/ml)

| | Totarol concentration | 0 h | | 8 h | | 16 h | | 24 h | |
|---|---|---|---|---|---|---|---|---|---|
| | | Inoculation cfu/ml | OD, average of 3 measurements | Inoculation cfu/ml | OD, average of 3 measurements | Inoculation cfu/ml | OD, average of 3 measurements | Inoculation cfu/ml | OD, average of 3 measurements |
| Stock I | 0.16% | $6 \times 10^5$ | 0.638 | 0 | 0.651 | 0 | 0.510 | 0 | 0.369 |
| Stock II | 0.08% | $3.2 \times 10^5$ | 0.448 | 0 | 0.539 | 0 | 0.499 | 0 | 0.491 |
| Stock III | 0.04% | $2.6 \times 10^5$ | 0.552 | 0 | 0.667 | 0 | 0.555 | 0 | 0.538 |
| | 0.02% | $3.1 \times 10^5$ | 0.322 | 0 | 0.384 | 0 | 0.374 | 0 | 0.371 |
| | 0.01% | $4.1 \times 10^5$ | 0.302 | 0 | 0.419 | 0 | 0.368 | 0 | 0.306 |

TABLE 1-continued

Determination of the MIC value of totarol against the *Enterococcus faecalis* strain.
*Enterococcus faecalis* - clinical strain
(initial working density 7.0 × 10$^5$ cfu/ml)

|  | Totarol concentration | 0 h | | 8 h | | 16 h | | 24 h | |
|---|---|---|---|---|---|---|---|---|---|
|  |  | Inoculation cfu/ml | OD, average of 3 measurements | Inoculation cfu/ml | OD, average of 3 measurements | Inoculation cfu/ml | OD, average of 3 measurements | Inoculation cfu/ml | OD, average of 3 measurements |
|  | 0.005% | 6 × 10$^5$ | 0.302 | 0 | 0.349 | 0 | 0.320 | 0 | 0.296 |
|  | 0.0025% | 5 × 10$^5$ | 0.284 | 0 | 0.297 | 0 | 0.295 | 0 | 0.302 |
|  | 0.0013% | 4 × 10$^5$ | 0.293 | 6 × 10$^4$ | 0.297 | 6 × 10$^4$ | 0.399 | 1 × 10$^7$ | 0.549 |
|  | 0.0007% | 2.5 × 10$^5$ | 0.288 | 3.1 × 10$^5$ | 0.291 | 3.8 × 10$^5$ | 0.445 | 2.1 × 10$^7$ | 0.602 |
|  | 0.0004% | 3 × 10$^5$ | 0.298 | 2.1 × 10$^5$ | 0.303 | 1.1 × 10$^6$ | 0.491 | 1.9 × 10$^7$ | 0.677 |
|  | 0.0002% | 4 × 10$^5$ | 0.292 | 4.1 × 10$^5$ | 0.295 | 2.1 × 10$^6$ | 0.490 | 1.6 × 10$^7$ | 0.681 |
| Bacterial broth | Positive control (I) | 7 × 10$^5$ | 0.238 | 6.2 × 10$^5$ | 0.381 | 6.2 × 10$^6$ | 0.531 | 3.1 × 10$^7$ | 0.659 |
| Bacterial broth + DMI | Positive control (II) | 8 × 10$^5$ | 0.206 | 6 × 10$^5$ | 0.313 | 4.9 × 10$^6$ | 0.470 | 2.1 × 10$^7$ | 0.648 |
| Broth + DMI | Negative control | 0 | 0.248 | 0 | 0.249 | 0 | 0.240 | 0 | 0.238 |

Appendix

Appendix

TABLE 2

Determination of the MIC value of totarol against the *Streptococcus agalactiae* strain.
*Streptococcus agalactiae* - clinical strain
(initial suspension density 1.0 × 10$^5$ cfu/ml)

|  | Totarol concentration | 0 h | | 8 h | | 16 h | | 24 h | |
|---|---|---|---|---|---|---|---|---|---|
|  |  | Inoculation cfu/ml | OD, average of 3 measurements | Inoculation cfu/ml | OD, average of 3 measurements | Inoculation cfu/ml | OD, average of 3 measurements | Inoculation cfu/ml | OD |
| Stock I | 0.16% | 2 × 10$^5$ | 0.512 | 0 | 0.605 | 0 | 0.569 | 0 | 0.615 |
| Stock II | 0.08% | 5 × 10$^5$ | 0.563 | 0 | 0.564 | 0 | 0.540 | 0 | 0.430 |
| Stock III | 0.04% | 3 × 10$^5$ | 0.406 | 0 | 0.535 | 0 | 0.489 | 0 | 0.405 |
|  | 0.02% | 10$^5$ | 0.318 | 0 | 0.323 | 0 | 0.324 | 0 | 0.324 |
|  | 0.01% | 10$^5$ | 0.297 | 0 | 0.295 | 0 | 0.301 | 0 | 0.307 |
|  | 0.005% | 1.5 × 10$^5$ | 0.288 | 0 | 0.292 | 0 | 0.296 | 0 | 0.300 |
|  | 0.0025% | 2.6 × 10$^5$ | 0.289 | 0 | 0.290 | 0 | 0.291 | 0 | 0.291 |
|  | 0.0013% | 3.3 × 10$^5$ | 0.299 | 0 | 0.302 | 0 | 0.302 | 0 | 0.302 |
|  | 0.0007% | 4.5 × 10$^5$ | 0.297 | 6 × 10$^4$ | 0.319 | 3.5 × 10$^6$ | 0.630 | 6 × 10$^7$ | 0.941 |
|  | 0.0004% | 6 × 10$^5$ | 0.305 | 6 × 10$^6$ | 0.318 | 9.1 × 10$^5$ | 0.493 | 2 × 10$^7$ | 0.668 |
|  | 0.0002% | 3.4 × 10$^5$ | 0.289 | 4 × 10$^6$ | 0.314 | 1.1 × 10$^6$ | 0.498 | 1 × 10$^7$ | 0.682 |
| Bacterial broth | Positive control (I) | 1.0 × 10$^5$ | 0.299 | 3 × 10$^7$ | 0.322 | 8 × 10$^7$ | 0.501 | 8 × 10$^7$ | 0.748 |
| Bacterial broth + DMI | Positive control (II) | 3 × 10$^5$ | 0.277 | 8 × 10$^7$ | 0.299 | 6 × 10$^7$ | 0.501 | 6 × 10$^7$ | 0.747 |
| Broth + DMI | Negative control | 0 | 0.333 | 0 | 0.344 | 0 | 0.330 | 0 | 0.343 |

Appendix

Appendix

TABLE 3

Determination of the MIC value of totarol against the *Gardnerella vaginalis* strain.
*Gardnerella vaginalis* - clinical strain
(initial suspension density $2.8 \times 10^5$ cfu/ml)

|  | Totarol concentration | 0 h | | 8 h | | 16 h | | 24 h | |
| --- | --- | --- | --- | --- | --- | --- | --- | --- | --- |
|  |  | Inoculation cfu/ml | OD, average of 3 measurements | Inoculation cfu/ml | OD, average of 3 measurements | Inoculation cfu/ml | OD, average of 3 measurements | Inoculation cfu/ml | OD, average of 3 measurements |
| Stock I | 0.16% | $1.4 \times 10^5$ | 0.822 | 0 | 0.564 | 0 | 0.451 | 0 | 0.438 |
| Stock II | 0.08% | $6.1 \times 10^5$ | 0.740 | 0 | 0.523 | 0 | 0.455 | 0 | 0.441 |
| Stock III | 0.04% | $3.7 \times 10^5$ | 0.460 | 0 | 0.416 | 0 | 0.411 | 0 | 0.379 |
|  | 0.02% | $2.1 \times 10^5$ | 0.344 | 0 | 0.332 | 0 | 0.333 | 0 | 0.334 |
|  | 0.01% | $1.6 \times 10^5$ | 0.319 | 0 | 0.323 | 0 | 0.325 | 0 | 0.328 |
|  | 0.005% | $3.1 \times 10^5$ | 0.318 | 0 | 0.318 | 0 | 0.323 | 0 | 0.327 |
|  | 0.0025% | $1.3 \times 10^5$ | 0.312 | $5 \times 10^4$ | 0.311 | $5.2 \times 10^4$ | 0.314 | $2.3 \times 10^4$ | 0.317 |
|  | 0.0013% | $1 \times 10^5$ | 0.321 | $2.7 \times 10^4$ | 0.314 | $6.2 \times 10^5$ | 0.318 | $1.2 \times 10^5$ | 0.322 |
|  | 0.0007% | $9 \times 10^4$ | 0.315 | $6 \times 10^4$ | 0.307 | $2.1 \times 10^5$ | 0.326 | $3.8 \times 10^5$ | 0.346 |
|  | 0.0004% | $2.2 \times 10^5$ | 0.326 | $2 \times 10^5$ | 0.334 | $4.9 \times 10^5$ | 0.362 | $3.9 \times 10^5$ | 0.390 |
|  | 0.0002% | $1.5 \times 10^5$ | 0.313 | $2 \times 10^5$ | 0.328 | $2 \times 10^5$ | 0.364 | $2.2 \times 10^5$ | 0.398 |
| Bacterial broth | Positive control (I) | $3 \times 10^5$ | 0.293 | $7 \times 10^5$ | 0.312 | $6.7 \times 10^6$ | 0.312 | $8 \times 10^6$ | 0.429 |
| Bacterial broth + DMI | Positive control (II) | $3 \times 10^5$ | 0.321 | $6 \times 10^5$ | 0.336 | $7.3 \times 10^6$ | 0.336 | $1.1 \times 10^7$ | 0.516 |
| Broth + DMI | Negative control | 0 | 0.342 | 0 | 0.333 | 0 | 0.312 | 0 | 0.323 |

Appendix

Appendix

TABLE 4

Determination of the MIC value of totarol against the *Lactobacillus plantarum* strain.
*Lactobacillus plantarum* - clinical strain
(initial suspension density $1.9 \times 10^5$ cfu/ml)

|  | Totarol concentration | 0 h | | 8 h | | 16 h | | 24 h | |
| --- | --- | --- | --- | --- | --- | --- | --- | --- | --- |
|  |  | Inoculation cfu/ml | OD, average of 3 measurements | Inoculation cfu/ml | OD, average of 3 measurements | Inoculation cfu/ml | OD, average of 3 measurements | Inoculation cfu/ml | OD |
| Stock I | 0.16% | $3.7 \times 10^5$ | 0.472 | $4 \times 10^4$ | 0.320 | $7.1 \times 10^4$ | 0.346 | $4.1 \times 10^4$ | 0.371 |
| Stock II | 0.08% | $3.2 \times 10^5$ | 0.401 | $1.2 \times 10^4$ | 0.413 | $3.5 \times 10^4$ | 0.368 | $5 \times 10^4$ | 0.357 |
| Stock III | 0.04% | $2.6 \times 10^5$ | 0.398 | $1.6 \times 10^5$ | 0.370 | $2.4 \times 10^5$ | 0.379 | $2.4 \times 10^5$ | 0.397 |
|  | 0.02% | $7.5 \times 10^5$ | 0.330 | $1.0 \times 10^5$ | 0.299 | $5.1 \times 10^6$ | 0.837 | $3.1 \times 10^7$ | 1.375 |
|  | 0.01% | $5.5 \times 10^5$ | 0.295 | $5 \times 10^5$ | 0.298 | $6.4 \times 10^6$ | 0.871 | $3.4 \times 10^7$ | 1.445 |
|  | 0.005% | $4.2 \times 10^5$ | 0.288 | $1.2 \times 10^5$ | 0.300 | $1.8 \times 10^6$ | 0.895 | $3.8 \times 10^7$ | 1.476 |
|  | 0.0025% | $2.8 \times 10^5$ | 0.284 | $1.0 \times 10^5$ | 0.303 | $8.4 \times 10^6$ | 0.914 | $1.4 \times 10^7$ | 1.552 |
|  | 0.0013% | $3.8 \times 10^5$ | 0.293 | $3.2 \times 10^5$ | 0.305 | $5.1 \times 10^6$ | 0.913 | $4.1 \times 10^7$ | 1.521 |
|  | 0.0007% | $6.5 \times 10^5$ | 0.292 | $4.5 \times 10^5$ | 0.300 | $8.1 \times 10^6$ | 0.902 | $5.1 \times 10^7$ | 1.504 |
|  | 0.0004% | $2.1 \times 10^5$ | 0.304 | $2 \times 10^5$ | 0.309 | $3.9 \times 10^6$ | 0.892 | $3.1 \times 10^7$ | 1.508 |
|  | 0.0002% | $3.9 \times 10^5$ | 0.291 | $3.5 \times 10^5$ | 0.305 | $4.2 \times 10^6$ | 0.854 | $2.9 \times 10^7$ | 1.469 |
| Bacterial broth | Positive control (I) | $1.9 \times 10^5$ | 0.324 | $6.1 \times 10^5$ | 0.317 | $6.2 \times 10^6$ | 0.939 | $3.2 \times 10^7$ | 1.560 |
| Bacterial broth + DMI | Positive control (II) | $1.7 \times 10^5$ | 0.308 | $3.5 \times 10^5$ | 0.303 | $2.9 \times 10^6$ | 0.851 | $2 \times 10^7$ | 1.397 |
| Broth + DMI | Negative control | 0 | 0.330 | 0 | 0.331 | 0 | 0.329 | 0 | 0.311 |

TABLE 5

Determination of the MIC value of totarol against the *Lactobacillus gasseri* strain.
*Lactobacillus gasseri* - clinical strain
(initial suspension density $1.4 \times 10^5$ cfu/ml)

| | Totarol concentration | 0 h Inoculation cfu/ml | 0 h OD, average of 3 measurements | 8 h Inoculation cfu/ml | 8 h OD, average of 3 measurements | 16 h Inoculation cfu/ml | 16 h OD, average of 3 measurements | 24 h Inoculation cfu/ml | 24 h OD |
|---|---|---|---|---|---|---|---|---|---|
| Stock I | 0.16% | $6.5 \times 10^5$ | 0.427 | $2.5 \times 10^4$ | 0.411 | $3.1 \times 10^1$ | 0.409 | $1 \times 10^1$ | 0.406 |
| Stock II | 0.08% | $2.9 \times 10^5$ | 0.526 | $1 \times 10^4$ | 0.409 | $1.9 \times 10^2$ | 0.463 | $1.2 \times 10^2$ | 0.472 |
| Stock III | 0.04% | $4.6 \times 10^5$ | 0.352 | $6 \times 10^4$ | 0.335 | $4.5 \times 10^3$ | 0.342 | $5 \times 10^3$ | 0.349 |
| | 0.02% | $1.4 \times 10^5$ | 0.305 | $1.4 \times 10^5$ | 0.299 | $2.1 \times 10^5$ | 0.753 | $1 \times 10^5$ | 1.208 |
| | 0.01% | $3.9 \times 10^5$ | 0.301 | $7 \times 10^4$ | 0.297 | $5.3 \times 10^6$ | 0.799 | $1.3 \times 10^7$ | 1.301 |
| | 0.005% | $1.2 \times 10^5$ | 0.292 | $2 \times 10^5$ | 0.300 | $9.1 \times 10^6$ | 0.843 | $2.1 \times 10^7$ | 1.387 |
| | 0.0025% | $4.5 \times 10^5$ | 0.285 | $1.5 \times 10^5$ | 0.302 | $2.3 \times 10^6$ | 0.880 | $2.3 \times 10^7$ | 1.459 |
| | 0.0013% | $3.8 \times 10^5$ | 0.298 | $1.8 \times 10^5$ | 0.301 | $4.1 \times 10^6$ | 0.879 | $2.1 \times 10^7$ | 1.457 |
| | 0.0007% | $1.7 \times 10^5$ | 0.289 | $1.9 \times 10^5$ | 0.299 | $3.6 \times 10^6$ | 0.879 | $3 \times 10^7$ | 1.458 |
| | 0.0004% | $5.1 \times 10^5$ | 0.296 | $2.1 \times 10^5$ | 0.306 | $3.9 \times 10^6$ | 0.915 | $3.2 \times 10^7$ | 1.484 |
| | 0.0002% | $3.1 \times 10^5$ | 0.299 | $2.1 \times 10^5$ | 0.302 | $5.9 \times 10^6$ | 0.897 | $2.9 \times 10^7$ | 1.492 |
| Bacterial broth | Positive control (I) | $1.4 \times 10^5$ | 0.293 | $4 \times 10^5$ | 0.307 | $1 \times 10^7$ | 0.885 | $1 \times 10^8$ | 1.463 |
| Bacterial broth + DMI | Positive control (II) | $1 \times 10^5$ | 0.297 | $1.4 \times 10^4$ | 0.307 | $9 \times 10^6$ | 0.776 | $9 \times 10^7$ | 1.246 |
| Broth + DMI | Negative control | 0 | 0.330 | 0 | 0.331 | 0 | 0.329 | 0 | 0.311 |

TABLE 6

Influence of the tested substance - totarol - on the apoptosis and necrosis phenomena of human cells of vaginal epithelium A-431.

| | Human vaginal epithelium line A-431 | | | | | | | | |
|---|---|---|---|---|---|---|---|---|---|
| | 2 h | | | 8 h | | | 24 h | | |
| Tested samples | Alive cells | Apopt. cells | Necrot. cells | Alive cells | Apopt. cells | Necrot. cells | Alive cells | Apopt. cells | Necrot. Cells |
| Totarol | 100 | 0 | 0 | 100 | 0 | 0 | 100 | 0 | 0 |
| Negative control | 100 | 0 | 0 | 100 | 0 | 0 | 99 | 0 | 1 |
| Solvent control | 100 | 0 | 0 | 99 | 0 | 1 | 97 | 0 | 3 |
| Necrosis positive control | 0 | 0 | 100 | 0 | 0 | 100 | 0 | 0 | 100 |

The invention claimed is:

1. A method for treatment of vaginal membrane inflammations of bacterial origin, for alleviation of symptoms in such a treatment, for prophylaxis and prevention of relapses of such inflammations, for treatment of anaerobic bacterial vaginosis (BV) and aerobic vaginitis (AV) comprising administering a pharmaceutical composition comprising totarol in an amount of 0.001 parts by weight (wt.) to 5.0 parts by wt. as an active agent.

2. A method for treatment of anaerobic bacterial vaginosis (BV) and aerobic vaginitis (AV), comprising: administering a pharmaceutical composition comprising totarol to a vaginal mucous membrane, wherein administering a pharmaceutical composition comprising totarol comprises administering a pharmaceutical composition including totarol in an amount of 0.001 parts by weight (wt.) to 5.0 parts by wt. as an active substance.

3. The method according to claim 2, wherein administering the pharmaceutical composition comprising totarol treats vaginal mucous membrane inflammations of bacterial origin, alleviates symptoms in such a treatment and provides prophylaxis and prevention of relapses of such inflammations.

4. The method according to claim 2, wherein administering the pharmaceutical composition comprising totarol limits disturbances in a composition of vaginal bacterial flora.

5. The method according to claim 2, wherein the pharmaceutical composition further comprises:
- from 75 parts by weight (wt.) to 95 parts by wt. of a cellulose derivative;
- from 0.5 parts by wt. to 5 parts by wt. of lactic acid; and
- from 0.5 parts by wt. to 5 parts by wt. of a basic polymer, wherein a stoichiometric ratio of lactic acid to the basic polymer is 1:1 to 8:1.

6. The method according to claim 5, wherein the cellulose derivative comprises methylcellulose.

7. The method according to claim d, wherein the basic polymer comprises at least one of the following: an acrylic polymer, a copolymer of methacrylic acid and ethyl acrylate, chitosan, polyvinylpyrrolidone or any combination thereof.

8. The method according to claim 2, wherein the pharmaceutical composition is in a powder form, in a gel form, in a molded pessaries form, or in a tablet form.

* * * * *